(12) United States Patent
Chandler (10) Patent No.: US 6,168,956 B1
(45) Date of Patent: *Jan. 2, 2001

(54) MULTIPLE COMPONENT CHROMATOGRAPHIC ASSAY DEVICE

(75) Inventor: Howard M. Chandler, W. Vancouver (CA)

(73) Assignee: Beckman Coulter, Inc., Fullerton, CA (US)

(*) Notice: Under 35 U.S.C. 154(b), the term of this patent shall be extended for 0 days.

This patent is subject to a terminal disclaimer.

(21) Appl. No.: 07/706,639

(22) Filed: May 29, 1991

(51) Int. Cl.$^7$ ................................................ G01N 33/558

(52) U.S. Cl. ........................ 436/514; 422/56; 422/57; 435/6; 435/7.1; 435/7.92; 435/7.93; 435/7.94; 435/7.95; 435/287.1; 435/287.2; 435/805; 435/810; 435/970; 436/518; 436/810

(58) Field of Search .................... 436/514, 501, 436/517, 518, 807, 808, 809, 810; 435/6, 7.1, 7.92, 7.93, 7.94, 7.95, 970, 287.1, 287.2, 805, 810; 422/58, 56, 57

(56) References Cited

U.S. PATENT DOCUMENTS

| | | | |
|---|---|---|---|
| Re. 30,267 | 5/1980 | Bruschi | 23/230 B |
| Re. 31,006 | 8/1982 | Schuurs et al. | 435/7 |
| 1,926,299 | 9/1933 | Monk | 206/45.29 |
| 3,078,031 | 2/1963 | Kauffeld | 229/208 |
| 3,186,623 | 6/1965 | Guyer | 229/204 |
| 3,307,770 | 3/1967 | Wysocki | 229/231 |
| 3,420,205 | 1/1969 | Morison . | |
| 3,437,449 | 4/1969 | Luckey . | |
| 3,475,129 | 10/1969 | Peurifoy et al. . | |
| 3,551,555 | 12/1970 | Schuurs . | |
| 3,720,760 | 3/1973 | Bennich et al. . | |

(List continued on next page.)

FOREIGN PATENT DOCUMENTS

| | | |
|---|---|---|
| 3130749 | 2/1983 | (DE) . |
| 0045476 | 2/1982 | (EP) . |
| 0068310 | 11/1982 | (EP) . |
| 0125118 | 11/1984 | (EP) . |
| 0154749 | 9/1985 | (EP) . |
| 0170746 | 2/1986 | (EP) . |
| 0183442 | 6/1986 | (EP) . |
| 0191640 | 8/1986 | (EP) . |
| 0217403 | 4/1987 | (EP) . |
| 0225054 | 6/1987 | (EP) . |
| 0227173 | 7/1987 | (EP) . |
| 0238012 | 9/1987 | (EP) . |
| 0250137 | 12/1987 | (EP) . |

(List continued on next page.)

OTHER PUBLICATIONS

Wilchek, et al., "The Avidin–Biotin Complex in Immunology", Immunology Today (1984), vol. 5, No. 2, pp. 39–43.

*Primary Examiner*—Christopher L. Chin
(74) *Attorney, Agent, or Firm*—William H. May; P. R. Harder; Merchant & Gould (57) ABSTRACT

An assay device for the performance of immunochromatographic assays and other assays has two principal parts, a first opposable component and a second opposable component. The first opposable component can contain a sample preparation means and a second opposable component can contain a suitable chromatographic medium for detection of an analyte. Alternative embodiments of the invention can also exist. For example, the first opposable component can have a sample preparation means and a chromatographic medium that is not in communication with the sample preparation means and the second opposable component can contain a communicating means that, when the two components are brought into opposition, establishes a communication between the sample preparation means and the chromatographic medium. Assay devices according to the present invention can be used for both unidirectional and bidirectional assays.

33 Claims, 3 Drawing Sheets

U.S. PATENT DOCUMENTS

| | | |
|---|---|---|
| 3,723,064 | 3/1973 | Liotta . |
| 3,798,004 | 3/1974 | Zerachia et al. . |
| 3,811,840 | 5/1974 | Bauer et al. . |
| 3,867,517 | 2/1975 | Ling . |
| 3,888,629 | 6/1975 | Bagshawe . |
| 3,893,808 | 7/1975 | Campbell . |
| 3,901,657 | 8/1975 | Lightfoot . |
| 3,902,964 | 9/1975 | Greenspan . |
| 3,915,647 | 10/1975 | Wright . |
| 3,926,564 | 12/1975 | Giaever . |
| 3,932,220 | 1/1976 | Liotta . |
| 3,933,594 | 1/1976 | Milligan et al. . |
| 3,933,997 | 1/1976 | Hersh et al. . |
| 3,935,074 | 1/1976 | Rubenstein et al. . |
| 3,949,064 | 4/1976 | Bornstein et al. . |
| 3,951,332 | 4/1976 | Torbeck ................ 229/241 |
| 3,960,499 | 6/1976 | White . |
| 3,961,894 | 6/1976 | Gordon . |
| 3,966,897 | 6/1976 | Renn et al. . |
| 3,975,162 | 8/1976 | Renn . |
| 3,979,509 | 9/1976 | Giaever . |
| 3,981,981 | 9/1976 | Reunanen . |
| 3,984,533 | 10/1976 | Uzgiris ................. 424/12 |
| 3,985,867 | 10/1976 | Redshaw ............... 424/1.5 |
| 3,989,591 | 11/1976 | Liotta ................... 195/1.8 |
| 3,990,850 | 11/1976 | Friedman .............. 23/230 B |
| 3,992,058 | 11/1976 | Przybylowicz et al. ......... 23/253 TP |
| 3,993,451 | 11/1976 | Verbeck ................ 23/253 R |
| 3,996,006 | 12/1976 | Pagano ................. 23/253 |
| 4,012,198 | 3/1977 | Finter et al. ............ 23/253 R |
| 4,016,043 | 4/1977 | Schuurs et al. ......... 195/103.5 R |
| 4,017,597 | 4/1977 | Reynolds ............... 424/1.5 |
| 4,018,662 | 4/1977 | Ruhenstroth-Bauer et al. 204/299 R |
| 4,020,151 | 4/1977 | Bolz et al. .............. 424/1.5 |
| 4,038,485 | 7/1977 | Johnston et al. ........ 23/230 B |
| 4,039,652 | 8/1977 | Adams et al. ........... 424/1 |
| 4,042,335 | 8/1977 | Clement ................ 23/253 TP |
| 4,046,514 | 9/1977 | Johnston et al. ......... 23/253 TP |
| 4,053,284 | 10/1977 | Posch .................... 23/259 |
| 4,054,646 | 10/1977 | Giaever ................. 424/12 |
| 4,059,407 | 11/1977 | Hochstrasser ........... 23/253 TP |
| 4,065,383 | 12/1977 | Skare et al. ............ 210/27 |
| 4,066,403 | 1/1978 | Bruschi ................. 23/230 B |
| 4,067,774 | 1/1978 | Rubenstein et al. ....... 195/63 |
| 4,067,959 | 1/1978 | Bolz ..................... 424/1 |
| 4,087,326 | 5/1978 | Kereluk ................ 195/103.5 R |
| 4,087,332 | 5/1978 | Hansen ................. 195/127 |
| 4,094,647 | 6/1978 | Deutsch et al. ......... 23/253 TP |
| 4,108,729 | 8/1978 | Mennen ................ 195/127 |
| 4,108,972 | 8/1978 | Dreyer .................. 424/1 |
| 4,108,976 | 8/1978 | Reese .................... 424/1 |
| 4,110,079 | 8/1978 | Schaeffer et al. ........ 23/253 TP |
| 4,116,638 | 9/1978 | Kenoff ................. 422/99 |
| 4,123,224 | 10/1978 | Givner et al. ........... 422/59 |
| 4,123,509 | 10/1978 | Banik et al. ............ 424/12 |
| 4,128,399 | 12/1978 | Liotta et al. ........... 23/230 B |
| 4,129,417 | 12/1978 | White .................. 23/230 B |
| 4,130,462 | 12/1978 | Rubenstein et al. ....... 195/103.5 A |
| 4,133,639 | 1/1979 | Harte ................... 23/230 B |
| 4,134,792 | 1/1979 | Boguslaski et al. ....... 159/99 |
| 4,144,306 | 3/1979 | Figueras ............... 422/56 |
| 4,145,186 | 3/1979 | Andersen ............... 22/232 R |
| 4,145,406 | 3/1979 | Schick et al. ........... 424/1 |
| 4,153,668 | 5/1979 | Hill et al. .............. 422/56 |
| 4,157,323 | 6/1979 | Yen et al. .............. 260/29.7 M |
| 4,160,008 | 7/1979 | Fenocketti et al. ....... 422/56 |
| 4,166,102 | 8/1979 | Johnson ................ 424/1 |
| 4,168,146 | 9/1979 | Grubb et al. ........... 23/230 B |
| 4,169,138 | 9/1979 | Jonsson ................ 424/12 |
| 4,175,923 | 11/1979 | Friend .................. 23/230 B |
| 4,177,253 | 12/1979 | Davies et al. ........... 424/1 |
| 4,180,383 | 12/1979 | Johnson . |
| 4,189,304 | 2/1980 | Adams, Jr. et al. ....... 23/230 B |
| 4,200,690 | 4/1980 | Root et al. ............. 435/7 |
| 4,205,058 | 5/1980 | Wagner et al. .......... 424/1 |
| 4,205,952 | 6/1980 | Cais ..................... 23/230 B |
| 4,210,418 | 7/1980 | Brown et al. ........... 23/230 B |
| 4,219,335 | 8/1980 | Ebersole ............... 23/230 B |
| 4,223,089 | 9/1980 | Rothe et al. ........... 435/12 |
| 4,228,237 | 10/1980 | Hevey et al. ........... 435/7 |
| 4,233,029 | 11/1980 | Columbus ............. 2/230 R |
| 4,233,402 | 11/1980 | Maggio et al. .......... 435/7 |
| 4,235,601 | 11/1980 | Deutsch et al. ......... 23/230 R |
| 4,237,234 | 12/1980 | Meunier ............... 435/301 |
| 4,238,565 | 12/1980 | Hornby et al. .......... 435/7 |
| 4,243,749 | 1/1981 | Sadeh et al. ........... 435/7 |
| 4,244,694 | 1/1981 | Farina et al. ........... 23/230 B |
| 4,246,339 | 1/1981 | Cole et al. ............. 435/7 |
| 4,248,829 | 2/1981 | Kitajima et al. ........ 422/56 |
| 4,248,965 | 2/1981 | Mochida et al. . |
| 4,254,082 | 3/1981 | Schick et al. ........... 422/55 |
| 4,254,083 | 3/1981 | Columbus ............. 422/55 |
| 4,255,384 | 3/1981 | Kitajuma et al. ........ 422/57 |
| 4,256,693 | 3/1981 | Kondo et al. ........... 422/56 |
| 4,258,001 | 3/1981 | Pierce et al. ........... 422/56 |
| 4,268,270 | 5/1981 | Gabbay et al. ......... 23/230.3 |
| 4,270,921 | 6/1981 | Graas .................. 23/230 B |
| 4,271,119 | 6/1981 | Columbus ............. 422/50 |
| 4,274,832 | 6/1981 | Wu et al. .............. 23/230 R |
| 4,275,149 | 6/1981 | Litman et al. .......... 435/7 |
| 4,279,617 | 7/1981 | Masson et al. ......... 23/23 B |
| 4,279,885 | 7/1981 | Reese et al. . |
| 4,280,816 | 7/1981 | Elahi et al. ............ 23/230 B |
| 4,281,061 | 7/1981 | Zuk et al. .............. 435/7 |
| 4,288,228 | 9/1981 | Oberhardt ............. 23/230 R |
| 4,298,345 | 11/1981 | Sodickson et al. ....... 23/230 R |
| 4,298,685 | 11/1981 | Parikh et al. .......... 435/7 |
| 4,299,916 | 11/1981 | Litman et al. .......... 435/6 |
| 4,301,139 | 11/1981 | Feingers et al. ........ 424/1 |
| 4,305,720 | 12/1981 | Bernstein ............. 23/230 B |
| 4,305,721 | 12/1981 | Bernstein ............. 23/230 B |
| 4,305,924 | 12/1981 | Piasio et al. ........... 424/1 |
| 4,313,734 | 2/1982 | Leuvering ............. 23/230 B |
| 4,315,907 | 2/1982 | Fridlender et al. ...... 424/1 |
| 4,318,707 | 3/1982 | Litman et al. .......... 23/230 B |
| 4,323,536 | 4/1982 | Columbus ............. 422/56 |
| 4,332,783 | 6/1982 | Pernice et al. .......... 424/1 |
| 4,333,733 | 6/1982 | Sanford et al. ......... 23/230 B |
| 4,337,065 | 6/1982 | Hiratsuka et al. ....... 23/230 B |
| 4,338,094 | 7/1982 | Elahi ................... 23/230 B |
| 4,347,312 | 8/1982 | Brown et al. ........... 435/7 |
| 4,357,311 | 11/1982 | Schutt .................. 424/12 |
| 4,361,537 | 11/1982 | Deutsch et al. ......... 422/56 |
| 4,362,697 | 12/1982 | Tabb et al. ............. 422/56 |
| 4,363,874 | 12/1982 | Greenquist ............ 435/7 |
| 4,365,970 | 12/1982 | Lawrence et al. ....... 436/66 |
| 4,366,241 | 12/1982 | Tom et al. ............. 435/7 |
| 4,373,932 | 2/1983 | Gribnau et al. ......... 436/501 |
| 4,374,925 | 2/1983 | Litman et al. .......... 435/7 |
| 4,376,110 | 3/1983 | David et al. ........... 436/513 |
| 4,380,580 | 4/1983 | Boguslaski et al. . |
| 4,390,343 | 6/1983 | Walter ................. 436/518 |
| 4,391,904 | 7/1983 | Litman et al. .......... 435/7 |
| 4,407,943 | 10/1983 | Cole et al. ............. 435/7 |
| 4,411,518 | 10/1983 | Meserol et al. . |
| 4,425,438 | 1/1984 | Bauman et al. ........ 436/527 |
| 4,426,451 | 1/1984 | Columbus ............. 436/518 |
| 4,427,769 | 1/1984 | Adlercreutz et al. .... 435/7 |
| 4,435,504 | 3/1984 | Zuk et al. .............. 435/7 |
| 4,442,204 | 4/1984 | Greenquist et al. ..... 435/7 |
| 4,444,193 | 4/1984 | Fogt et al. ............. 128/632 |

| | | | | | | | |
|---|---|---|---|---|---|---|---|
| 4,446,232 | 5/1984 | Liotta | 435/7 | 4,797,260 | 1/1989 | Parker | 422/101 |
| 4,447,526 | 5/1984 | Rupchock et al. | 435/7 | 4,803,048 | 2/1989 | Nason | 422/58 |
| 4,447,529 | 5/1984 | Greenquist et al. | 435/7 | 4,803,154 | 2/1989 | Uo et al. | 435/7 |
| 4,447,546 | 5/1984 | Hirschfeld | 436/527 | 4,803,170 | 2/1989 | Stanton et al. | 436/518 |
| 4,450,231 | 5/1984 | Ozkan | 435/7 | 4,806,311 | 2/1989 | Greenquist | 422/56 |
| 4,452,901 | 6/1984 | Gordon et al. | 436/506 | 4,806,312 | 2/1989 | Greenquist | 422/56 |
| 4,459,358 | 7/1984 | Berke | 436/17 | 4,810,470 | 3/1989 | Burkhardt et al. | 422/56 |
| 4,461,829 | 7/1984 | Greenquist et al. | 435/7 | 4,812,293 | 3/1989 | McLaurin et al. | 422/69 |
| 4,464,552 | 8/1984 | Pawlowski | 206/569 | 4,814,142 | 3/1989 | Gleisner | 422/56 |
| 4,472,498 | 9/1984 | Masuda et al. | 437/7 | 4,816,224 | 3/1989 | Vogel et al. | 422/55 |
| 4,474,878 | 10/1984 | Halbert et al. | 435/7 | 4,818,677 | 4/1989 | Hay-Kaufman et al. | 435/4 |
| 4,477,575 | 10/1984 | Vogel et al. | 436/170 | 4,826,759 * | 5/1989 | Guire et al. | 435/4 |
| 4,486,530 | 12/1984 | David et al. | 435/7 | 4,837,145 | 6/1989 | Liotta | 435/7 |
| 4,504,585 | 3/1985 | Reynolds | 436/518 | 4,837,168 | 6/1989 | de Jaeger | 436/533 |
| 4,506,009 | 3/1985 | Lenhoff et al. | 435/7 | 4,837,373 | 6/1989 | Gunkel et al. | 422/56 |
| 4,514,507 | 4/1985 | Secher | 436/518 | 4,837,395 | 6/1989 | Leeder et al. | 435/7 |
| 4,517,288 | 5/1985 | Giegel et al | 435/7 | 4,843,000 | 6/1989 | Litman et al. | 435/7 |
| 4,533,629 | 8/1985 | Litman et al. | 435/7 | 4,847,199 | 7/1989 | Synder et al. | 435/36 |
| 4,540,659 | 9/1985 | Litman | 435/7 | 4,849,338 | 7/1989 | Litman et al. | 435/7 |
| 4,550,075 | 10/1985 | Bacquet et al. | 435/7 | 4,849,340 | 7/1989 | Oberhardt | 435/13 |
| 4,552,839 | 11/1985 | Gould et al. | 435/7 | 4,851,210 | 7/1989 | Hewett | 424/11 |
| 4,562,148 | 12/1985 | Sommer | 435/7 | 4,851,356 | 7/1989 | Canfield et al. . | |
| 4,582,811 | 4/1986 | Pucci et al. | 436/548 | 4,853,335 | 8/1989 | Olsen et al. | 436/527 |
| 4,594,327 | 6/1986 | Zuk | 436/514 | 4,855,240 | 8/1989 | Rosenstein et al. | 436/514 |
| 4,604,365 | 8/1986 | O'Neill et al. | 436/528 | 4,857,453 | 8/1989 | Ullman et al. | 435/7 |
| 4,608,336 | 8/1986 | Benovic et al. | 435/7 | 4,859,603 | 8/1989 | Dole et al. | 435/287 |
| 4,613,567 | 9/1986 | Yasoshima et al. | 435/7 | 4,859,612 | 8/1989 | Cole et al. | 436/523 |
| 4,615,983 | 10/1986 | Koyama | 436/514 | 4,861,711 | 8/1989 | Friesen et al. | 436/7 |
| 4,623,461 | 11/1986 | Hossom et al. | 210/445 | 4,868,106 | 9/1989 | Ito et al. | 435/7 |
| 4,629,690 | 12/1986 | Weng et al. | 435/7 | 4,868,108 | 9/1989 | Bahar et al. | 435/7 |
| 4,631,174 | 12/1986 | Kondo | 422/56 | 4,870,005 | 9/1989 | Akiyoshi et al. | 435/7 |
| 4,632,901 | 12/1986 | Valkirs et al. | 435/5 | 4,874,692 | 10/1989 | Eikenberry | 435/7 |
| 4,639,419 | 1/1987 | Olson et al. | 435/5 | 4,876,067 | 10/1989 | Deneke et al. | 422/56 |
| 4,642,285 | 2/1987 | Halbert et al. | 435/7 | 4,877,586 | 10/1989 | Devaney, Jr. et al. | 422/101 |
| 4,656,129 | 4/1987 | Wagner . | | 4,879,215 | 11/1989 | Weng et al. | 435/7 |
| 4,663,278 | 5/1987 | NiNello | 435/7 | 4,880,751 | 11/1989 | Georghegan | 436/518 |
| 4,666,866 | 5/1987 | Krauth . | | 4,883,764 | 11/1989 | Kloepfer | 436/63 |
| 4,668,619 | 5/1987 | Greenquist et al | 435/7 | 4,889,816 | 12/1989 | Davis et al. | 436/518 |
| 4,678,757 | 7/1987 | Rapkin et al. | 436/169 | 4,900,663 | 2/1990 | Wie et al. | 435/7 |
| 4,681,782 | 7/1987 | Ozkan | 428/36 | 4,902,629 | 2/1990 | Meserol et al. | 436/165 |
| 4,683,197 | 7/1987 | Gallati | 435/7 | 4,904,583 | 2/1990 | Mapes et al. . | |
| 4,687,732 | 8/1987 | Ward et al. | 435/6 | 4,912,034 | 3/1990 | Kalra et al. | 435/7 |
| 4,687,735 | 8/1987 | DiNello et al. | 435/7 | 4,916,056 | 4/1990 | Brown, III et al. | 435/7 |
| 4,690,907 | 9/1987 | Hibino et al. | 436/514 | 4,916,078 | 4/1990 | Klose et al. | 436/165 |
| 4,693,834 | 9/1987 | Hossom | 210/767 | 4,918,025 | 4/1990 | Grenner | 436/165 |
| 4,703,017 | 10/1987 | Campbell et al. | 436/501 | 4,920,045 | 4/1990 | Okuda et al. | 435/7 |
| 4,711,955 | 12/1987 | Ward et al. | 536/29 | 4,920,046 | 4/1990 | McFarland et al. | 435/7 |
| 4,717,656 * | 1/1988 | Swanljung | 435/7.92 | 4,923,680 | 5/1990 | Nelson | 422/58 |
| 4,722,906 | 2/1988 | Guire | 436/501 | 4,931,385 | 6/1990 | Block et al. | 435/7 |
| 4,727,019 | 2/1988 | Valkirs et al. | 435/5 | 4,933,092 | 6/1990 | Aunet et al. . | |
| 4,738,823 | 4/1988 | Engelmann | 422/56 | 4,938,927 | 7/1990 | Kelton et al. | 422/64 |
| 4,740,468 | 4/1988 | Weng et al. | 435/7 | 4,939,098 | 7/1990 | Suzuki et al. | 436/514 |
| 4,742,011 | 5/1988 | Blake et al. | 436/518 | 4,943,522 | 7/1990 | Eisinger et al. | 435/7 |
| 4,742,560 | 5/1988 | Campbell et al. | 436/501 | 4,952,517 | 8/1990 | Bahar | 436/518 |
| 4,752,562 | 6/1988 | Sheiman et al. | 435/5 | 4,952,520 | 8/1990 | Okusa et al. | 436/533 |
| 4,753,893 | 6/1988 | Roper | 436/509 | 4,956,275 | 9/1990 | Zuk et al. | 435/7 |
| 4,754,024 | 6/1988 | Roper | 436/507 | 4,956,302 | 9/1990 | Gordon et al. | 436/161 |
| 4,757,002 | 7/1988 | Joo . | | 4,959,197 | 9/1990 | Parekh et al. | 422/101 |
| 4,760,142 | 7/1988 | Primes et al. | 544/287 | 4,959,305 | 9/1990 | Woodrum | 435/7 |
| 4,761,381 | 8/1988 | Blatt et al. | 436/165 | 4,959,307 | 9/1990 | Olson | 435/7 |
| 4,770,853 | 9/1988 | Bernstein | 422/58 | 4,960,565 | 10/1990 | Shurben | 422/61 |
| 4,774,174 | 9/1988 | Giegel et al. | 435/5 | 4,960,691 | 10/1990 | Gordon et al. | 435/6 |
| 4,775,636 | 10/1988 | Moeremans et al. | 436/518 | 4,960,692 | 10/1990 | Lentrichia et al. | 435/7 |
| 4,776,612 | 10/1988 | Cox | 283/1 A | 4,963,325 | 10/1990 | Lennon et al. | 422/61 |
| 4,780,280 | 10/1988 | Berger et al. | 422/56 | 4,963,468 | 10/1990 | Olson | 435/7 |
| 4,782,016 | 11/1988 | Norton | 435/21 | 4,976,926 | 12/1990 | Matkovich | 422/101 |
| 4,786,594 | 11/1988 | Khanna et al. | 435/7 | 4,977,078 | 12/1990 | Niimura et al. | 435/7 |
| 4,788,136 | 11/1988 | Grenier et al. | 435/7 | 4,981,786 | 1/1991 | Dafforn et al. | 435/7 |
| 4,789,526 | 12/1988 | Matkovich | 422/101 | 4,988,627 | 1/1991 | Smith-Lewis | 436/165 |
| 4,789,629 | 12/1988 | Baker et al. | 435/7 | 4,990,442 | 2/1991 | Del Campo | 435/7.5 |
| 4,790,979 | 12/1988 | Terminiello et al. | 422/56 | 4,999,285 | 3/1991 | Stiso | 435/7.9 |

| | | | |
|---|---|---|---|
| 4,999,287 | 3/1991 | Allen et al. ............................. 435/11 |
| 5,006,464 | 4/1991 | Chu et al. ............................. 435/7.1 |
| 5,006,474 | 4/1991 | Horstman et al. .................... 436/524 |
| 5,009,996 | 4/1991 | Shah et al. .............................. 435/7 |
| 5,009,997 | 4/1991 | Shah et al. ............................ 435/7.4 |
| 5,024,323 | 6/1991 | Bolton ................................. 206/63.3 |
| 5,028,535 | 7/1991 | Buechler et al. ..................... 435/7.1 |
| 5,030,555 | 7/1991 | Clemmons ............................... 435/5 |
| 5,030,558 | 7/1991 | Litman et al. ....................... 435/7.91 |
| 5,039,607 | 8/1991 | Skold et al. .......................... 435/7.5 |
| 5,051,237 | 9/1991 | Grenner et al. ....................... 422/56 |
| 5,059,526 | 10/1991 | Arai et al. ............................. 435/17 |
| 5,064,541 | 11/1991 | Jeng et al. . |
| 5,071,746 | 12/1991 | Wilk et al. .......................... 435/7.94 |
| 5,073,484 | 12/1991 | Swanson et al. .................... 435/7.92 |
| 5,075,078 | 12/1991 | Osikowicz et al. .................... 422/56 |
| 5,079,142 | 1/1992 | Coleman et al. .................... 435/7.92 |
| 5,079,172 | 1/1992 | Hari et al. ............................. 436/518 |
| 5,079,174 | 1/1992 | Buck et al. .......................... 436/538 |
| 5,085,978 | 2/1992 | Olson ................................. 435/7.91 |
| 5,085,988 | 2/1992 | Olson ................................. 435/7.91 |
| 5,087,556 | 2/1992 | Ertinghausen ........................ 435/7.9 |
| 5,089,391 | 2/1992 | Buechler et al. ..................... 435/7.1 |
| 5,094,962 | 3/1992 | Snyder et al. ........................ 436/518 |
| 5,096,809 | 3/1992 | Chen et al. ............................ 435/7.9 |
| 5,096,837 | 3/1992 | Fan et al. ............................. 436/514 |
| 5,100,619 | 3/1992 | Baker et al. ............................ 422/58 |
| 5,100,620 | 3/1992 | Brenneman ............................ 422/58 |
| 5,104,793 | 4/1992 | Buck ................................... 435/7.92 |
| 5,104,811 | 4/1992 | Berger et al. ......................... 436/164 |
| 5,104,812 * | 4/1992 | Kurn et al ............................. 436/165 |
| 5,106,582 | 4/1992 | Baker ..................................... 422/58 |
| 5,106,758 | 4/1992 | Adler et al. .......................... 436/165 |
| 5,110,550 | 5/1992 | Schlipfenbacher et al. ........... 422/56 |
| 5,114,673 | 5/1992 | Berger et al. .......................... 422/56 |
| 5,114,862 | 5/1992 | Brenneman .......................... 436/169 |
| 5,119,941 | 6/1992 | Lepie .................................... 206/102 |
| 5,120,643 | 6/1992 | Ching et al. ......................... 435/7.92 |
| 5,120,662 | 6/1992 | Chan et al. ........................... 436/530 |
| 5,132,086 | 7/1992 | Allen et al. ............................. 422/56 |
| 5,132,208 | 7/1992 | Freitag et al. ......................... 435/7.1 |
| 5,135,716 | 8/1992 | Thakore ................................. 422/56 |
| 5,135,872 | 8/1992 | Pouletty et al. ...................... 436/180 |
| 5,135,873 | 8/1992 | Patel et al. ........................... 436/180 |
| 5,137,804 | 8/1992 | Greene et al. ........................... 435/5 |
| 5,137,808 | 8/1992 | Ullman et al. ........................ 435/7.9 |
| 5,141,850 * | 8/1992 | Cole et al. ............................ 436/525 |
| 5,141,875 | 8/1992 | Kelton et al. ......................... 436/514 |
| 5,143,210 | 9/1992 | Warwick ............................ 206/45.13 |
| 5,145,784 | 9/1992 | Cox et al. ............................. 436/526 |
| 5,156,952 | 10/1992 | Litman et al. ....................... 435/7.91 |
| 5,158,869 | 10/1992 | Pouletty et al. ....................... 435/7.9 |
| 5,158,895 | 10/1992 | Ashihara et al. ..................... 436/526 |
| 5,160,486 | 11/1992 | Schlipfenbacher et al. ........... 422/56 |
| 5,162,237 | 11/1992 | Messenger et al. .................. 436/523 |
| 5,164,294 | 11/1992 | Skold et al. .......................... 435/7.5 |
| 5,177,021 | 1/1993 | Kondo .................................. 436/518 |
| 5,182,191 | 1/1993 | Fan et al. ............................... 435/7.9 |
| 5,182,216 | 1/1993 | Clayton et al. ....................... 436/518 |
| 5,185,127 | 2/1993 | Vonk ...................................... 422/56 |
| 5,188,939 | 2/1993 | Mangold et al. .................... 435/7.92 |
| 5,188,966 | 2/1993 | Eikmeier et al. ..................... 436/170 |
| 5,202,267 | 4/1993 | Ditlow et al. ......................... 436/525 |
| 5,202,268 | 4/1993 | Kuhn et al. ........................... 436/525 |
| 5,206,177 | 4/1993 | DeLaCroix et al. ................. 436/518 |
| 5,209,904 | 5/1993 | Forney et al. .......................... 422/73 |
| 5,211,914 | 5/1993 | Vogel et al. ............................ 422/56 |
| 5,212,060 | 5/1993 | Maddox . |
| 5,215,886 | 6/1993 | Patel et al. ............................. 435/11 |
| 5,223,436 | 6/1993 | Freitag et al. ......................... 436/97 |
| 5,232,835 | 8/1993 | Litman et al. ....................... 435/7.93 |
| 5,234,813 | 8/1993 | McGeehan et al. .................. 435/7.9 |
| 5,236,826 | 8/1993 | Marshall .............................. 435/7.92 |
| 5,238,652 | 8/1993 | Sun et al. ............................... 422/61 |
| 5,240,862 | 8/1993 | Koenhen et al. . |
| 5,248,619 | 9/1993 | Skold et al. .......................... 435/514 |
| 5,252,492 | 10/1993 | Yoshikami .......................... 436/501 |
| 5,256,372 | 10/1993 | Brooks et al. ......................... 422/58 |
| 5,258,163 | 11/1993 | Krause et al. .......................... 422/58 |
| 5,260,193 | 11/1993 | Olson ................................. 435/7.91 |
| 5,260,194 | 11/1993 | Olson ................................. 435/7.91 |
| 5,260,222 | 11/1993 | Patel et al. ........................... 436/180 |
| 5,264,180 | 11/1993 | Allen et al. ............................. 422/56 |
| 5,275,785 | 1/1994 | May et al. .............................. 422/56 |
| 5,294,369 | 3/1994 | Shigekawa et al. .............. 252/313.1 |
| 5,356,785 | 10/1994 | McMahon et al. ................. 435/7.92 |
| 5,656,503 | 8/1997 | May et al. . |

FOREIGN PATENT DOCUMENTS

| | | |
|---|---|---|
| 0259157 | 3/1988 | (EP) . |
| 0262328 | 4/1988 | (EP) . |
| 0267724 | 5/1988 | (EP) . |
| 0269362 | 6/1988 | (EP) . |
| 0269876 | 6/1988 | (EP) . |
| 0271204 | 6/1988 | (EP) . |
| 0323605 | 7/1988 | (EP) . |
| 0277723 A1 | 8/1988 | (EP) . |
| 0279097 | 8/1988 | (EP) . |
| 0284232 | 9/1988 | (EP) . |
| 0290921 | 11/1988 | (EP) . |
| 0291194 | 11/1988 | (EP) . |
| 0296724 | 12/1988 | (EP) . |
| 0297292 | 1/1989 | (EP) . |
| 0299359 A2 | 1/1989 | (EP) . |
| 0299428 | 1/1989 | (EP) . |
| 0306772 | 3/1989 | (EP) . |
| 0 310 406 | 4/1989 | (EP) . |
| 0309883 | 4/1989 | (EP) . |
| 0317001 | 5/1989 | (EP) . |
| 0 319 294 | 6/1989 | (EP) . |
| 0322340 | 6/1989 | (EP) . |
| 0 327 395 | 9/1989 | (EP) . |
| 0339450 | 11/1989 | (EP) . |
| 0342771 | 11/1989 | (EP) . |
| 0 351 248 | 1/1990 | (EP) . |
| 0374684 | 6/1990 | (EP) . |
| 0383619 | 8/1990 | (EP) . |
| 0407904 | 1/1991 | (EP) . |
| 0415679 | 3/1991 | (EP) . |
| 2016687A | 9/1979 | (GB) . |
| 2204398A | 11/1988 | (GB) . |
| WO84/02193 | 6/1984 | (WO) . |
| WO86/03839 | 7/1986 | (WO) . |
| WO86/04683 | 8/1986 | (WO) . |
| WO87/02774 | 5/1987 | (WO) . |
| WO87/02778 | 5/1987 | (WO) . |
| WO88/05540 | 7/1988 | (WO) . |
| WO89/03992 | 5/1989 | (WO) . |
| WO 89/06799 | 7/1989 | (WO) . |
| WO89/06801 | 7/1989 | (WO) . |
| WO90/05906 | 5/1990 | (WO) . |
| WO91/01003 | 1/1991 | (WO) . |

* cited by examiner

MULTIPLE COMPONENT CHROMATOGRAPHIC ASSAY DEVICE

FIELD OF THE INVENTION

This invention relates to chromatographic assay devices. In particular, this invention relates to chromatographic assay devices which are used to qualitatively or quantitatively test for the presence of clinically important biological molecules.

BACKGROUND OF THE INVENTION

Chromatographic assay systems are well-known and frequently used analytical systems. These assay systems have a wide range of utilities. Recently, they have taken on an ever larger role in providing physicians with information to guide the diagnosis and treatment of a variety of disorders.

Among the most important of such systems are the "thin layer" systems in which a solvent moves across a thin, flat, absorbent medium.

The use of immunoassays as a means of testing for the presence and amount of clinically important molecules has been known for some time. As long ago as 1956, J. M. Singer reported the use of an immune based latex agglutination test for detecting a factor associated with rheumatoid arthritis (Singer, J. M., Plotz, C. M., *Am. J. Med.* Vol. 22, pp 888–82). These techniques are used in a particularly popular form of chromatographic assays, known as immunochromatography. In their simplest forms, these tests use a disclosing reagent or particle which has been linked to an antibody to the molecule of interest. This combination is then mixed with the specimen and, if the molecule of interest is present, the disclosing reagent-linked antigens agglutinate with the molecule of interest, thereby giving an indication that the molecule of interest is present. The disclosing reagent or particle may be identifiable on the basis of color, magnetic properties, radioactivity or any number of other physical or chemical properties. The specific reactions which are employed vary with the nature of the molecule of interest and the sample which is to be tested.

Immunochromatographic assays fall into two principal categories: "sandwich" and "competitive". Generally, "sandwich-type" immunochromatographic procedures call for mixing a sample containing a molecule of interest with antibodies to that molecule, which causes an antigen-antibody complex to be formed. The antibodies which are used in this procedure are typically linked to a disclosing molecule or reagent, such as dyed latex, colloidal gold or a radioisotope. This mixture is then applied to a chromatographic medium which contains a band or zone to which antibodies to the molecule of interest have also applied. This medium often takes the form of a device or strips which resembles a "dipstick." When the complex of the molecule of interest and the antibodies with disclosing reagents or particles reaches the zone of the chromatographic medium with the antibodies, binding occurs and the bound disclosing particles or reagents are localized at the zone or band on the chromatographic medium. This indicates the presence of the molecule of interest in the sample. Quantitative results can sometimes be obtained in this manner.

In addition to immunochromatographic assays, it is also known to use enzyme-based chromatographic assays. These techniques are roughly analogous to immune-reaction based systems, but use an enzymatically catalyzed reaction instead of an antigen-antibody reaction. Other analogous chromatographic assays are also known.

The chromatographic techniques which are available to the clinician are not without their drawbacks. Sometimes the specimen which is to be tested contains cells or particulate matter which can add colors to the chromatographic medium thereby making it difficult to read the test. In some cases, such as tests using fecal samples, particulate matter within the sample can clog the pores of the chromatographic medium making immunochromatography very difficult, if not completely impossible. It is also important (and sometimes quite difficult) to apply the sample to the chromatographic medium so that the sample front will be applied to and move through the chromatographic medium and reach the area where binding is to occur in a uniform, straight-line manner.

Other problems associated with chromatographic devices and techniques which are available to the physician are those of sample preparation and waste generation. It is rarely possible to apply a sample (such as feces) or a sampling device (such as throat swab) directly to the chromatographic media. Several extraction and pretreatment reactions are usually required before the sample can be applied to the chromatographic medium. Conventionally, these preparatory steps are carried out by the physician or a technician in several small vessels, each of which (along with a transfer device, such as a pipette) is thereby contaminated with biological, chemical or radiological wastes, all of which can come into contact with the physician, technician and many others.

Another limitation on the chromatographic devices which are available to the clinician is their inability to perform 2 directional or 2 dimensional chromatography. These chromatographic techniques have long been known to be powerful analytical tools but their complexity relative to simple unidirectional chromatography has made it difficult to apply them in the physician's office.

SUMMARY OF THE INVENTION

In a chromatographic device according to the present invention there are two principal parts, a first and a second opposable component. The first opposable component contains a sample preparation means and the second opposable component contains a suitable chromatographic medium. In operation, a sample is placed on the sample preparation means (along with suitable reagents and solvents) and the sample is thereby prepared for application to the chromatographic mechanism, but is not applied to the chromatographic medium until after the preparatory reactions have taken place. The two opposable components are then brought into opposition, thereby bringing the sample preparation means on the first component into contact with the chromatographic medium on the second component. This applies the treated sample to the chromatographic medium and the chromatographic process then begins. The result can be observed via an appropriate opening or transparent portion of the device.

In another embodiment of the invention, the first opposable component has a sample preparation means and a chromatographic medium which is not in communication with the sample preparation means. The second opposable component contains a communicating means which, when the two components are brought into opposition, establishes a communication between the sample preparation means and the chromatographic medium. In use, the sample is applied to the sample preparation means and the required preparatory reactions are conducted. Once this is accomplished, the two components are brought into opposition and the chromatography is begun.

By locking the two opposed components of the device together, one can permanently encase the sample as well as all materials which have been exposed to the sample or to the chemical, biological or radiological materials used in the assay.

The two opposable components can be constructed of any material which provides suitable mechanical support or the desired degree of protection from the materials which are used in the test. The sample preparation means and the chromatographic medium will necessarily be adapted to the requirements of the particular assay which is to be performed. In an advantageous embodiment, the sample preparation means is an absorbent pad which can retain a suitable quantity of fluid and which has a pore size which allows the absorbent pad to filter out particulate matter which should not be applied to the chromatographic medium.

This unique construction provides a simple, self-contained device which permits the reliable execution of chromatographic assays by persons having only basic laboratory skills and without the risk or expense associated with the generation or leakage of biological, chemical or radiological wastes. This device also facilitates the sequential execution of pretreatment and chromatographic steps in a self-contained device.

This invention also provides a simple device which makes it possible to routinely conduct two directional or two dimensional chromatography in the physician's office.

DETAILED DESCRIPTION OF THE INVENTION

Figure 1A:
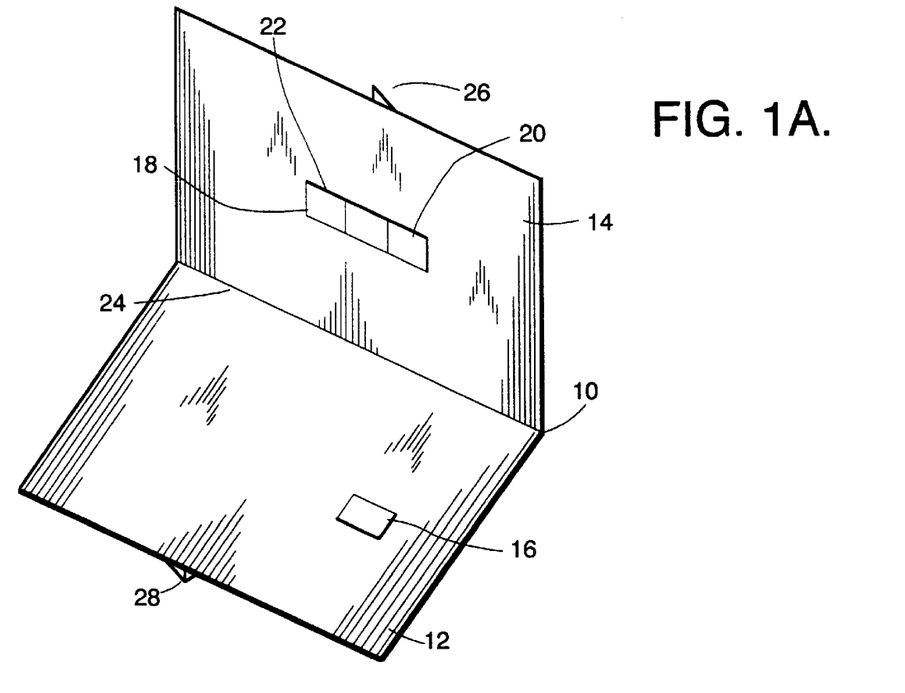
FIG. 1A is a drawing of a chromatographic assay device according to the present invention with a first opposable component and a second opposable component in which the first component includes a sample preparation means and the second opposable component includes a chromatographic medium, shown in open position.

A chromatographic assay device 10 according to the present invention is shown in FIG. 1A. It has a first opposable component 12 and a second opposable component 14.

The first component 12 includes a sample preparation means 16. Preferably, sample preparation means 16 is an absorbent pad which, besides serving as the locus of preparatory reactions which may be required, will serve to apply the treated sample to the chromatographic medium 18 on the second opposable component 14. Sample preparation means 16 can be made of any suitable material, such as cellulose, paper, nylon or non-woven synthetic fabrics. If filtration of particulate matter is desired, as in the case of whole blood or fecal samples, this function will be governed by the pore size of the material, which can be selected accordingly. A sample or, optionally, a sampling device, can be placed by the operator upon the sample preparation means 16 and appropriate reagents can be added. If desired, some or all of the reagents for the treatment of the sample can be made part of the sample preparation means 16, such as by impregnation in an absorbent pad.

The chromatographic medium 18 on the second opposable component 14 is comprised of suitable material such as nitrocellulose, nylon or silica. The chromatographic medium 18 can be pre-treated or modified to suit the needs of the assay which is to be performed. For example, when the device is to be used to perform a "sandwich" immunochromatography, zone 20 of the chromatographic medium 18 can be impregnated with antibodies, usually to the molecule of interest, which will serve to facilitate binding with those molecules and which may be bound to antibodies which are in turn attached to disclosing particles or reagents.

Optionally, the chromatographic medium 18 may include other zones which will serve as controls for the assay procedure. An example of such a control zone is zone 22 of FIG. 1A, to which a small amount of the molecule of interest (or a cross-reactant) has been applied. Labeled antibodies to the molecule of interest will agglutinate zone 22, thereby demonstrating that an absence of agglutination in zone 20 is not attributable to a lack of labeled antibodies in the sample which is applied to the device 10 in an immunochromatographic assay.

The bodies of opposable components 12 and 14 are preferably made of plastic which is impervious to moisture. In the embodiment which is shown in FIG. 1A, components 12 and 14 are joined by a hinge 24 and have locking means 26 and 28 which are engaged when the two components are brought into opposition. A sealing ridge or gasket 30 may be provided around the perimeter of the opposable components 12 and 14 to guard against leakage of samples or reagents.

Figure 1B:
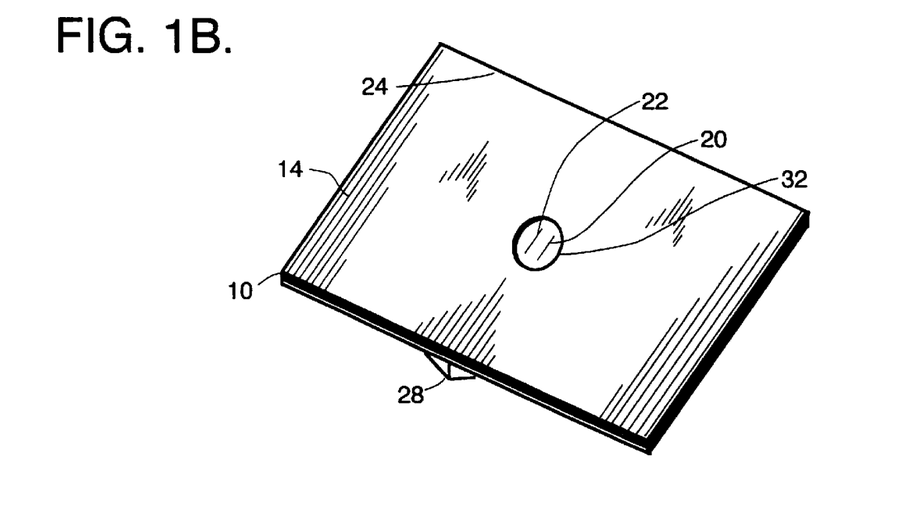
FIG. 1B is a drawing of the chromatographic assay device of FIG. 1A shown in closed position.

FIG. 1B shows device 10 after the opposable components 12 and 14 have been brought into opposition. The chromatographic medium 18 (including zones 20 and 22) is visible through window 32.

The present invention will now be described by reference to the following non-limiting examples.

EXAMPLE 1

A Strep B assay was performed in the following manner.

A device such as is shown in FIGS. 1A and 1B was provided with a sample preparation means which was adapted to receive a throat swab. A throat swab from a patient was placed on the sample preparation means and wetted with a suitable extraction reagent. After a suitable interval, an absorbent pad impregnated with anti-Strep B antibodies labeled with pink colloidal gold was added to the sample preparation means. The components were then brought into opposition so that the absorbent pad in the sample preparation means was brought into contact with the chromatographic medium on the second opposable component, thereby allowing the sample (including the labeled antigen/antibody complex) to migrate up the chromatographic medium. A band of the chromatographic medium was provided with anti-Strep B antigens and, when the sample reached this band, binding of the labeled complex occurred in that region, indicating the presence of Strep B antigen.

In a variation of this procedure, the impregnated absorbent pad can be placed in the second opposable component and brought into contact with the swab when the two components are brought into opposition. In another variation, the absorbent pad can be eliminated altogether and the labeled antibodies can be added to the swab as a liquid suspension and the swab can be used to apply the sample to the chromatographic medium when the two components are brought into opposition.

EXAMPLE 2

A bi-directional immunochromatographic assay for antibodies to *H. pylori* was performed in the following manner.

Figure 2A:
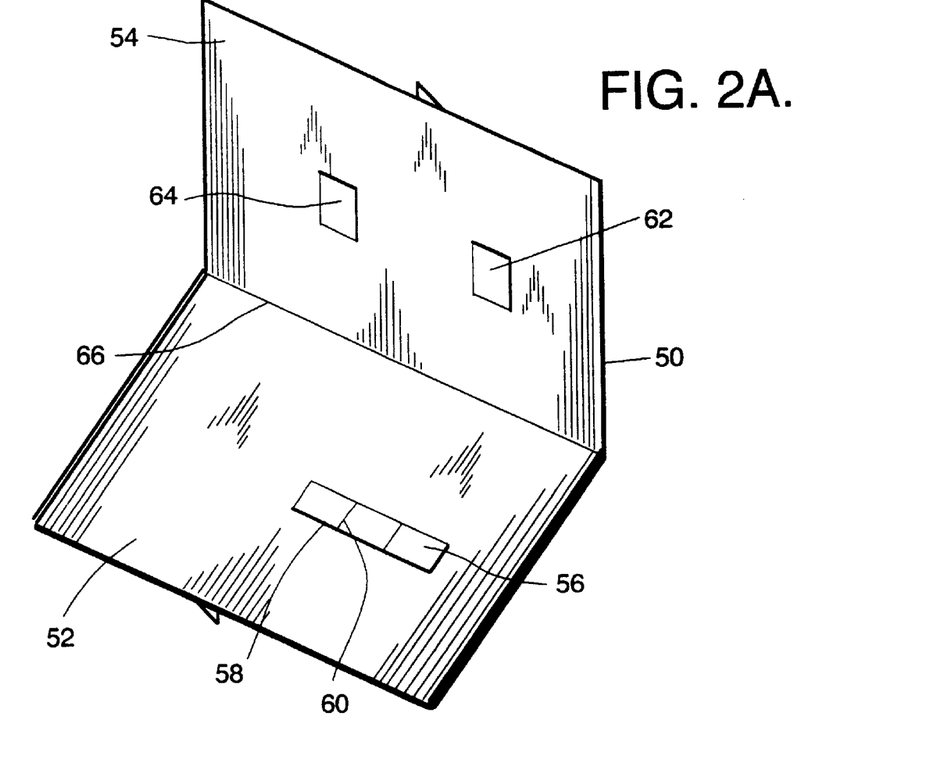
FIG. 2A is a drawing of an assay device for performing a bidirectional immunochromatographic assay for an antibody, shown in open position.

An assay device 50, as shown in FIG. 2A, having a first opposable component 52 and a second opposable component 54, was used. The first opposable component 52 included a first sample preparation means 56 which was in contact with one end of the chromatographic medium 58. The chromatographic medium 58 was made of nitrocellulose and included a zone 60 at which were immobilized specific antigen of *H. pylori*. The second opposable component 54 included an absorbent pad 62 and a second sample preparation means 64.

The serum specimen to be tested for the presence of antibodies to *H. pylori* was placed on the first sample preparation means 56 and thereby applied to the chromatographic medium 58. As the serum sample migrated up the chromatographic medium 58, antibodies specific to *H. pylori* antigen reacted with the antigen immobilized in zone 60 and were retained in that zone. A suspension of anti-human IgG antibody labelled with pink colloidal gold was then placed on the second sample preparation means 64, and the two opposable components were brought into opposition by closing hinge 66 which joined the two components. The device then appeared as in FIG. 2B.

Figure 2B:
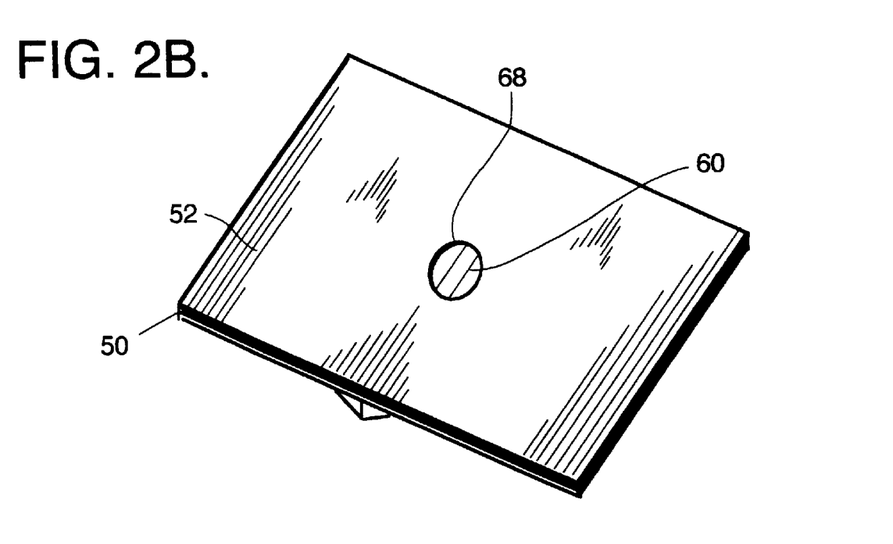
FIG. 2B is a drawing of the assay device of FIG. 2A in closed position.

When the two components were brought into opposition, the absorbent pad 62 was brought into contact with the first sample preparation 56 and drew the serum sample out of the first sample preparation means 56 and the chromatographic medium 58. Simultaneously, the second sample preparation means 64 was brought into contact with the opposite end of the chromatographic medium 58, thereby applying the solution of labeled anti-human IgG to the chromatographic medium 58. This caused a reversal of flow along the chromatographic medium 58 with the serum sample flowing back toward the first sample preparation means 56, followed by the labelled anti-human IgG antibodies. As the labelled anti-human IgG antibodies reached zone 60, they were bound to that zone, which resulted in a colored strip which was visible through window 68 and indicated the presence of *H. pylori* antibody.

EXAMPLE 3

An assay for fecal occult blood was conducted as follows.

A fecal sample was collected in a conventional manner by having a patient smear a specimen card with feces.

In a conventional assay procedure, the card would be placed in a solution which extracts hemoglobin, the extraction solution would then be filtered and then the filtered solution would be tested for the presence of hemoglobin. Besides its obvious aesthetic drawbacks, this procedure requires the use of a filter, an extraction vessel and a transfer pipette, all of which present disposal and/or sterilization problems. This also presents an unavoidable risk of spillage with resulting contamination.

By using an assay device according to the present invention, the use of ancillary vessels and the attendant contamination disposal problems were virtually eliminated.

The sample card was placed on the sample preparation means of a device such as is shown in FIGS. 1A & 1B. The sample preparation means included an absorbent pad made of cellulose. A quantity of extraction solution containing dye-labeled anti-human hemoglobin antibodies was also added to the sample preparation means and was allowed to extract hemoglobin from the sample for about one minute. The device was then closed and the extraction solution, along with the extracted hemoglobin which was bound to the dye labeled antibodies, migrated up the nitrocellulose chromatographic mechanism. The particulate matter in the feces was filtered out by the cellulose and was not applied to the chromatographic medium. As the hemoglobin migrated up the nitrocellulose, it reached a zone to which anti-human hemoglobin antibodies were immobilized and the labelled hemoglobin was localized in that zone. The resulting band of color indicated the presence of fecal occult blood.

This assay was accomplished without any extraneous vessels and the test device completely encased all specimens and reagents, greatly reducing the possibility of exposure to these materials and any infectious agents which they may contain.

EXAMPLE 4

Figure 3A:
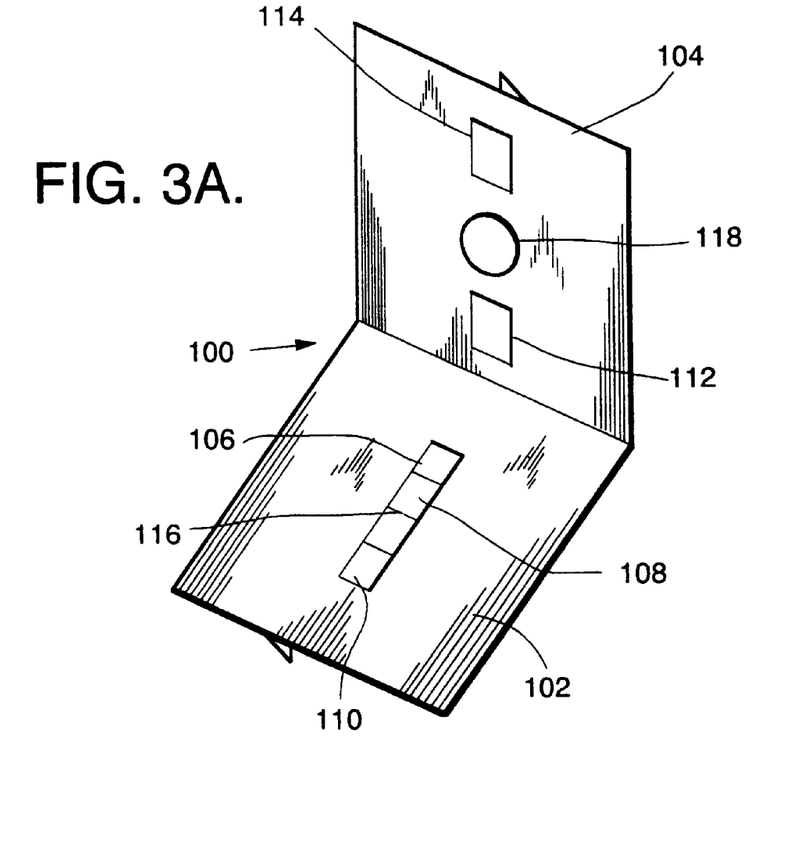
FIG. 3A is a drawing of a chromatographic assay device for the detection of *Helicobacter pylori* antibodies.
Figure 3B:
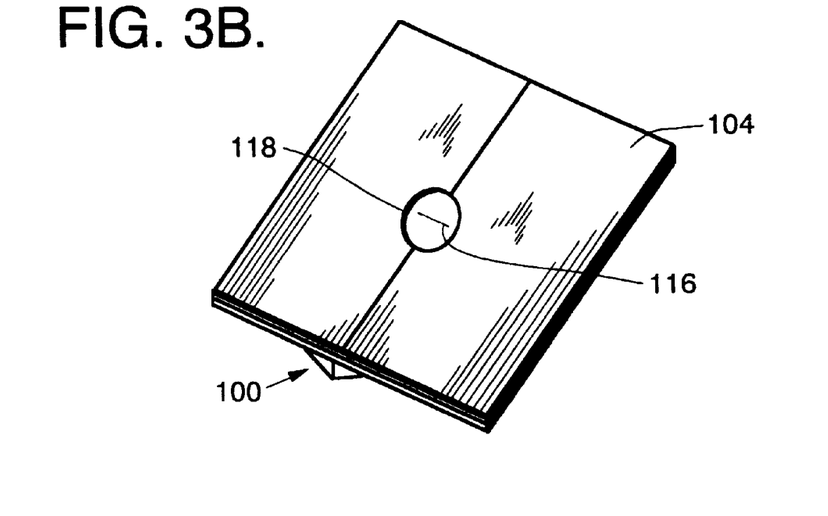
FIG. 3B is a drawing of the assay device of FIG. 3A in closed position showing the band visible through a window that indicates the presence of antibody.

An assay for the presence of *H. pylori* antibodies was conducted using a device 100 as shown in FIGS. 3A and 3B. The device has first and second opposable components 102 and 104. The first opposable component 102 contains a first application pad 106 which has been impregnated with an inert dye. Adjacent to and in communication with first application pad 106 is a nitrocellulose chromatographic medium 108. At the end of the chromatographic medium which is opposite to the first application pad 106 is a reagent-impregnated reagent pad 110. The reagents which are impregnated on the reagent pad 110 include anti-human IgG antibodies which have been labeled with pink colloidal gold. The second opposable component 104 contains an absorbent pad 112 and a second application pad 114.

In operation, a buffer solution was added to the second application pad 114 and the serum which was to be tested was added to the first application pad 106. The serum sample migrated across the chromatographic medium 108 and, as was indicated by the progress of the inert dye, passed zone 116 of the chromatographic medium 108. (*H. pylori* antigen had previously been immobilized in zone 116.) After this occurred, the two components were brought into opposition and the absorbent pad 112 was brought into contact with the first application pad 106, thereby causing the flow of the serum along the chromatographic medium 108 to be reversed. This also brought the second application pad 114 into contact with the reagent pad 110 and caused the buffer solution to be applied to the chromatographic medium 108 along with the labeled antibody reagent. When the buffer solution reached zone 116, the labeled antibody bound to the anti-*H. pylori* antibody that was itself bound to the *H. pylori* antigen that was located at the Zone 116, causing a pink band to develop, indicating the presence of anti-*H. pylori* antibody. The pink band in zone 116 was visible through window 118 as shown in FIG. 3B.

While the foregoing examples have described a variety of sample preparation procedures which can be performed in a device according to this invention, these examples are not an exhaustive listing of such procedures. In addition to sample dilution or the addition of extraction reagents or labels, it is possible to macerate tissue in a properly configured sample preparation means, such as by mechanical action before or after the components of the device are brought into opposition.

The assay device of the present invention is especially well suited to running several chromatograms simultaneously, a significant advantage when a quantitative or semi-quantitative assay is required.

What is claimed is:

1. A chromatographic assay device comprising:

a first opposable component including a sample preparation means for receiving a liquid sample to be assayed and containing a labeled mobile reagent to bind specifically to an analyte to be detected; and a second opposable component including a chromatographic medium having at least one reagent binding specifically to an analyte to be detected, the reagent being bound at a detection zone on the chromatographic medium, the second opposable component being connected to the first opposable component;

wherein the first and second opposable components can be brought into opposition by direct manual closure from a position in which they are not in opposition so as to cause the sample preparation means to apply the liquid sample to be tested to the chromatographic medium and to cause the liquid sample to flow through the chromatographic medium, the chromatographic assay being performed as a result of migration of the sample within the chromatographic medium so that the analyte is detected within the chromatographic medium as a result of the migration by binding of the labeled mobile reagent, the analyte being detected at a position different than the position at which the sample is applied to the chromatographic medium, the analyte being detected on the chromatographic medium after migration by binding of the labeled mobile reagent to the analyte bound to the detection zone.

2. The device of claim 1 wherein the sample preparation means includes at least one reagent for the treatment of the sample before the sample is applied to the chromatographic medium.

3. The device of claim 2 wherein the first and second opposable components each further comprise engaging means which secure the first and second opposable components in opposition.

4. The device of claim 3 wherein the first and second opposable components are joined by a hinge.

5. The device of claim 1 wherein the first and second opposable components are each substantially planar.

6. A chromatographic assay device comprising:

a first opposable component, including (1) a sample preparation means for receiving a liquid sample to be assayed and (2) a chromatographic medium which is not in communication with the sample preparation means and having at least one reagent binding specifically to an analyte to be detected, the reagent being bound at a detection zone on the chromatographic medium; and a second opposable component including a connecting member for transferring fluid from the sample preparation means to the chromatographic medium; wherein the first and second opposable components can be brought into opposition by direct manual closure from a position in which they are not into opposition so as to cause the connecting member to establish a communication between the sample preparation means and the chromatographic medium so as to result in the application of the liquid sample to the chromatographic medium through the connecting member and in flow of the sample through the chromatographic medium, the chromatographic assay being performed in the detection zone as a result of migration of the sample within the chromatographic medium so that the analyte is detected within the chromatographic medium as the result of migration, the analyte being detected at a position different than the position at which the sample is applied to the chromatographic medium, the analyte being detected on the chromatographic medium at the detection zone by binding of a labeled mobile reagent that binds specifically to the analyte to be detected.

7. The device of claim 6 wherein the sample preparation means includes at least one reagent for the treatment of the sample before the sample is applied to the chromatographic medium.

8. The device of claim 7 wherein the first and second opposable components each further comprise engaging means which secure the first and second opposable components in opposition.

9. The device of claim 8 wherein the first and second opposable components are joined by a hinge.

10. The device of claim 6 wherein the first and second opposable components are hingedly connected.

11. The device of claim 6 wherein the first and second opposable components are each substantially planar.

12. A chromatographic assay device for detecting the presence of *H. pylori* antibodies in a sample comprising:

a first opposable component including: (i) a chromatographic medium having first and second ends and a reagent that specifically binds *H. pylori* antibodies, the reagent being bound at a detection zone on the chromatographic medium and (ii) a first application means at the first end of the chromatographic medium, the detection zone being located between the first application means and the second end of the chromatographic medium; and a second opposable component including a second application means and an absorbing means;

wherein addition of a first liquid sample to the first application means causes a first liquid sample to flow from the first end of the chromatographic medium toward the second end of the chromatographic medium; and wherein bringing the first and second opposable components into opposition: (1) causes the second application means to come into contact with the second end of the chromatographic medium so as to apply a second liquid to the second end of the chromatographic medium, said second liquid containing a labeled mobile reagent that specifically binds *H. Pylori* antibodies, and (2) causes the absorbing means to come into contact with the first application means so as to withdraw fluid from the chromatographic medium via the first application means, thus reversing the flow in the chromatographic medium, the chromatographic assay being performed as a result of migration of the sample within the chromatographic medium so that *H. pylori* antibodies are detected as the result of the migration of the sample in a first direction within the chromatographic medium and of the second liquid applied to the chromatographic medium in a second direction opposite to the first direction, the *H. pylori* antibodies being detected at a position different than the position at which the sample is applied to the chromatographic medium by binding of the labeled mobile reagent to the *H. pylori* antibodies bound to the detection zone.

13. The chromatographic assay device of claim 12 wherein said labeled mobile reagent that binds *H. pylori* antibodies comprises anti-human IgG antibodies labeled with pink colloidal gold.

14. The device of claim 12 wherein the first and second opposable components are joined by a hinge.

15. The device of claim 12 wherein the first and second opposable components are each substantially planar.

16. The device of claim 12 wherein said first and second opposable components are each substantially of paper board construction.

17. A method for detecting an analyte in a liquid sample using a chromatographic medium having a first end and second end with a detection zone located between said first end and said second end, said detection zone comprising an immobilized antigen for said analyte, said method comprising:

applying said sample to said first end of said chromatographic medium whereby said sample migrates toward said second end of said chromatographic medium into said detection zone and said analyte binds to said immobilized antigen to form an immobilized analyte, applying to said second end of said chromatographic medium a solution containing labeled antibody reagent that binds to said analyte, whereby said solution migrates toward said first end of said chromatographic medium into said detection zone and said labeled antibody reagent binds to said immobilized analyte, permitting detection of said analyte.

18. The method of claim 17 wherein said chromatographic medium is substantially planar.

19. The method of claim 17 wherein said analyte is *H. pylori* antibodies.

20. The method of claim 17 wherein said labeled antibody reagent comprises anti-human IgG antibodies labeled with pink colloidal gold.

21. A method for detecting an analyte in a liquid sample using a chromatographic medium having (a) a first end and second end with a detection zone located between said first end and said second end, said detection zone comprising an immobilized antigen for said analyte, and (b) a labeled antibody reagent that binds to said analyte impregnated on said second end of said chromatographic medium, said method comprising:

applying said sample to said first end of said chromatographic medium whereby said sample migrates toward said second end of said chromatographic medium into said detection zone and said analyte binds to said immobilized antigen to form an immobilized analyte, applying a liquid migrating agent to said second end of said chromatographic medium whereby said liquid migrates, along with said labeled antibody reagent, toward said first end of said chromatographic medium into said detection zone and said labeled antibody reagent binds to said immobilized analyte, permitting detection of said analyte.

22. The method of claim 21 wherein said chromatographic medium is substantially planar.

23. The method of claim 21 wherein said analyte is *H. pylori* antibodies.

24. The method of claim 21 wherein said labeled antibody reagent comprises anti-human IgG antibodies labeled with pink colloidal gold.

25. The method of claim 21 wherein said first end of said chromatographic medium is impregnated with an inert dye.

26. A chromatographic assay device comprising:

a first opposable component including: (i) a chromatographic medium having first and second ends and a reagent that specifically binds an analyte to be detected, the reagent being bound at a detection zone on the chromatographic medium, (ii) a first application means impregnated with an inert dye adjacent to and in communication with the first end of the chromatographic medium, and (iii) a reagent pad impregnated with a labeled antibody reagent adjacent to and in communication with the second end of the chromatographic medium, the detection zone being located between the first application means and the reagent pad; and a second opposable component including a second application means containing a buffer solution and an absorbing means; wherein addition of a first liquid sample to the first application means causes the first liquid sample and the inert dye to flow from the first end of the chromatographic medium toward the second end of the chromatographic medium; and wherein bringing the first and second opposable components into opposition:

(1) causes the second application means containing the buffer solution to come into contact with the reagent pad so as to apply the buffer solution and labeled antibody reagent to the second end of the chromatographic medium and (2) causes the absorbing means to come into contact with the first application means so as to withdraw fluid from the chromatographic medium via the first application means, thus reversing the flow in the chromatographic medium, the chromatographic assay being performed as a result of migration of the sample and inert dye within the chromatographic medium so that an analyte is detected as the result of the migration of the sample and inert dye in a first direction within the chromatographic medium and of the buffer solution and labeled antibody reagent applied to the chromatographic medium in a second direction opposite to the first direction, the analyte being detected at a position different than the position at which the sample and inert dye are applied to the chromatographic medium by binding of the labeled reagent to the analyte bound to the detection zone.

27. The device of claim 26 wherein the first and second opposable components each further comprise engaging means which secure the first and secondopposable components in opposition.

28. The device of claim 27 wherein the first and second opposable components are joined by a hinge.

29. The device of claim 26 wherein the first and second opposable components are joined by a hinge.

30. The device of claim 26 wherein the first and second opposable components are each substantially planar.

31. The device of claim 26 wherein the second opposable component further includes a window for viewing the detection zone when the first and second opposable components are in opposition.

32. The device of claim 26 wherein said reagent analyte bound at a detection zone comprises *H. pylori* antigen.

33. The device of claim 26 wherein said labeled antibody reagent comprises anti-human IgG labeled with pink colloidal gold.

* * * * *